United States Patent
Takagi

[11] Patent Number: 6,082,860
[45] Date of Patent: Jul. 4, 2000

[54] OPHTHALMIC APPARATUS

[75] Inventor: Akinari Takagi, Tokyo, Japan

[73] Assignee: Kabushiki Kaisha Topcon, Tokyo, Japan

[21] Appl. No.: 09/378,272

[22] Filed: Aug. 20, 1999

[30]  Foreign Application Priority Data

Sep. 4, 1997  [JP]  Japan ................................. 9-239224
Aug. 21, 1998  [JP]  Japan ............................... 10-235677

[51] Int. Cl.[7] .................................................. A61B 3/14
[52] U.S. Cl. ............................................................ 351/208
[58] Field of Search ................................. 351/205, 211, 351/212, 215, 208, 221; 606/4, 5

[56]  References Cited

U.S. PATENT DOCUMENTS 5,988,815  11/1999  Maus et al. ............................. 351/221
5,997,529  11/1999  Tang et al. .................................. 606/4

FOREIGN PATENT DOCUMENTS 07023907  1/1995  Japan ................................ A61B 3/13

*Primary Examiner*—George Manuel
*Attorney, Agent, or Firm*—Chapman & Cutler

[57]  ABSTRACT

An ophthalmic apparatus having a main unit detects the alignment of the main unit with the subject's eye with respect to vertical and lateral directions by an XY-alignment detecting means on the basis of an index light beam projected on the eye and reflected from the cornea of the eye, detects the alignment of the main unit with the eye with respect to horizontal directions parallel to the optical axis of the eye by a Z-alignment detecting means on the basis of a Z-alignment index light beam projected obliquely on the eye and reflected from the cornea of the eye, and permits a display means to display the results of detection made by the Z-alignment detecting by a display permitting means when a predetermined condition is satisfied.

1 Claim, 5 Drawing Sheets

OPHTHALMIC APPARATUS

BACKGROUND OF THE INVENTION

1. Field of the Invention

The present invention relates to an ophthalmic apparatus which comprises an alignment detecting system, such as a non-contact tonometer, a keratometer or a corneal endothelium photographing apparatus.

More particularly, the present invention relates to an ophthalmic apparatus which projects an index light beam from an oblique direction onto the cornea of the eye to be examined, receives the light beam reflected on the cornea with a photoelectric element, and measures positional relation between the eye and the apparatus with respect to the Z-direction (forward and backward direction) based on the output of the photoelectric element.

2. Description of the Related Art

In the aforementioned known apparatus, an error is introduced into the result of Z-alignment measurement, if dislocation with respect to the XY direction (rightward/leftward, upward/downward) exists.

In order to solve the problem, an ophthalmic apparatus proposed in JP-A No. Hei 7-23907 has an error correcting system for correcting the result of Z-alignment measurement based on an XY alignment dislocation of a main unit from a correct position.

However, the ophthalmic apparatus described in JP-A No. Hei 7-23907 needs to store the measured XY-alignment dislocation, and calculate an accurate Z-alignment dislocation based on the stored XY-alignment dislocation. Accordingly, it takes considerable time to output an accurate Z-alignrent dislocation data.

If so-called flick movement occurs, the eye moves while calculating an accurate Z-alignment dislocation, so that it is difficult to accomplish the alignment.

SUMMARY OF THE INVENTION

Accordingly, it is an object of the present invention to provide an ophthalmic apparatus not requiring any operation for correcting measured data on the position of the ophthalmic apparatus relative to the eye, and capable of aligning itself with the eye in a short time.

According to one aspect of the present invention, an ophthalmic apparatus comprises:

a main unit;

an XY-alignment index light projecting means for projecting an alignment index light beam onto an eye;

an XY-alignment detecting means for detecting the alignment between the main unit and the eye with respect to lateral and vertical directions on the basis of the XY-alignment index light beam reflected from the cornea of the eye;

a z-alignment index light projecting means for obliquely projecting a Z-alignment index light beam onto the eye;

a Z-alignment detecting means for detecting the alignment between the main unit and the eye with respect to a horizontal direction parallel to the optical axis of the eye on the basis of the Z-alignment index light beam;

a display means for displaying measured results measured by the Z-alignment detecting means; and a display permitting means for permitting the display means to display information.

Since the measurement with respect to directions along the Z-axis need not be corrected, the main unit can quickly be aligned with the eye, and the measurement of the eye can be achieved without being affected by the small involuntary movement of the eye.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

An ophthalmic apparatus in a preferred embodiment according to the present invention will be described with reference to the accompanying drawings. The ophthalmic apparatus in this embodiment is a tonometer.

Figure 1:
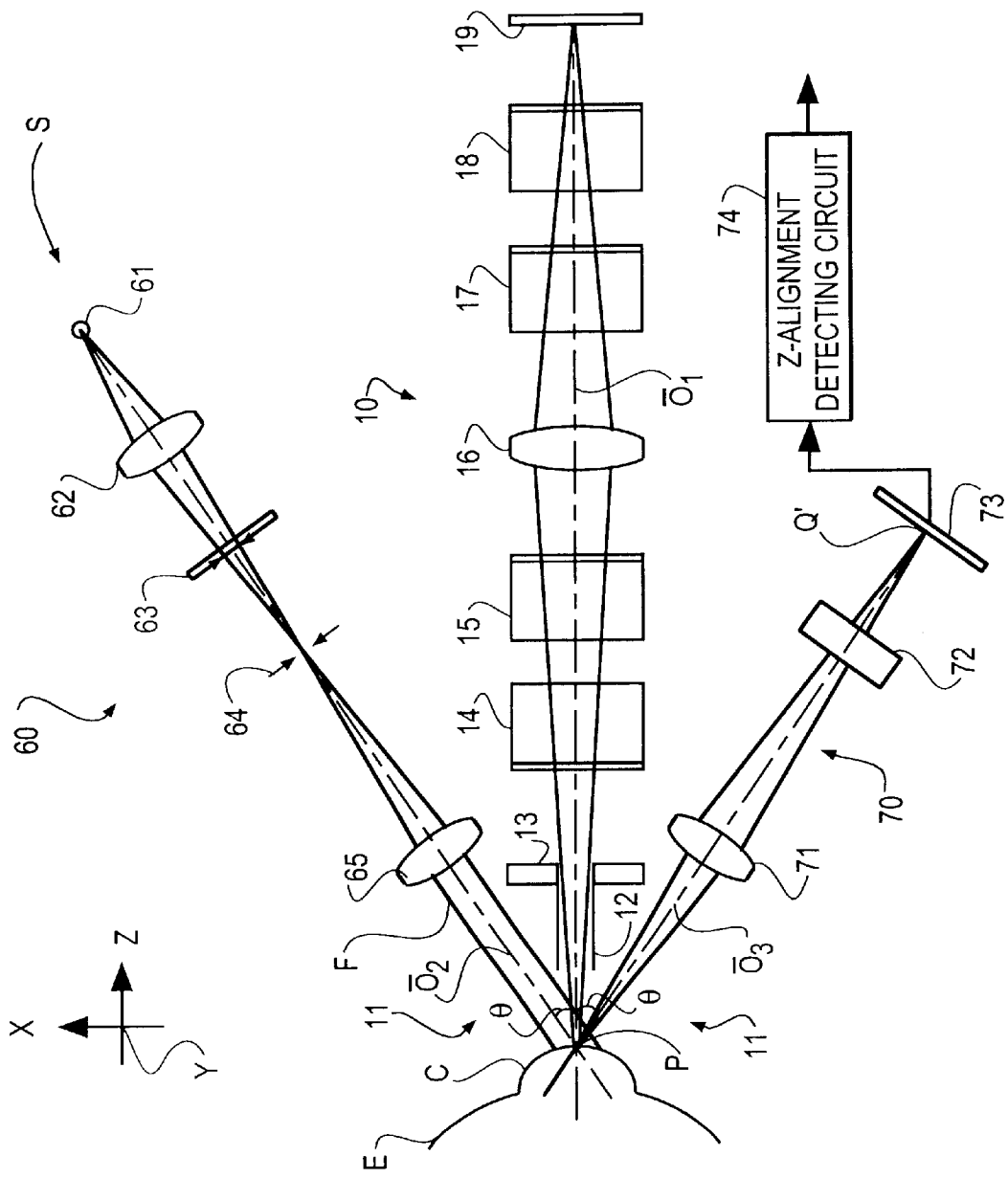
FIG. 1 is a diagrammatic plan view of an essential part of an optical system included in an ophthalmic apparatus in a preferred embodiment according to the present invention.
Figure 2:
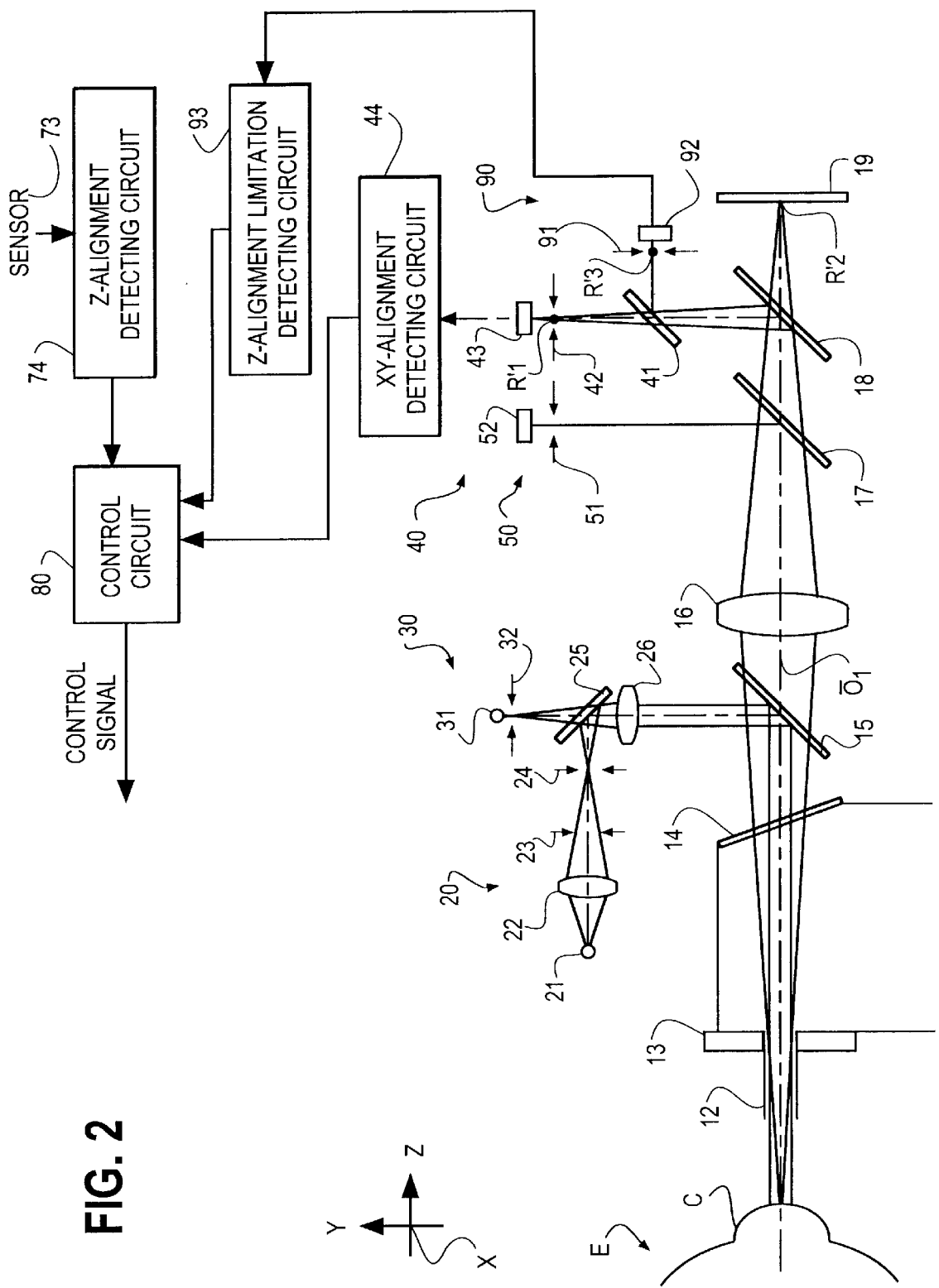
FIG. 2 is a diagrammatic side elevation of the optical system of the ophthalmic apparatus shown in FIG. 1, including a block diagram of a circuit.

Referring to FIGS. 1 and 2, a main unit S of the tonometer comprises an anterior segment observation system 10 for observing the anterior segment of the eye E, an XY-alignment index projecting optical system 20 for projecting on the cornea C of the subject's eye E an index light beam for alignment detection in X- and Y-directions, a fixation target projecting optical system 30 for projecting a fixation target on the eye E, an XY-alignment light beam detecting optical system 40 which receives a reflected XY-alignment index light beam reflected on the cornea C to determine the positional relation between the main unit S and the cornea C with respect to the X- and Y-direction, a cornea deformation detecting optical system 50 which receives the reflected XY-alignment index light beam reflected from the cornea C and determines the deformation of the cornea C, a Z-alignment index projecting optical system 60 for projecting an index light beam obliquely on the cornea C, a Z-alignment detecting optical system 70 for determining the positional relation between the main unit S and the cornea C with respect to the Z-direction by receiving the Z-alignment index light beam reflected from the cornea C from a direction symmetrical with the optical axis of the Z-alignment index projecting optical system 60 with respect to the optical axis of the anterior segment observation optical system 10, and a Z-alignment limitation detecting optical system 90 for detecting whether dislocation AX along the X-direction is less than the predetermined value. The XY-alignment index projecting optical system 20 and the XY-alignment detecting optical system 40 constitute an XY-alignment detecting unit. The Z-alignment index projecting optical system 60 and the Z-alignment detecting optical system 70 constitute a Z-alignment detecting unit.

The anterior segment observation optical system 10 has a plurality of illuminating light sources 11 disposed on the right and the left sides of the eye E to illuminate the eye E directly, a puffing nozzle 12, an anterior segment glass plate 13, a chamber glass plate 14, a semitransparent mirror 15, an objective 16, semitransparent mirrors 17 and 18 and a CCD camera 19. The anterior segment observation optical system 10 has an optical axis $O_1$.

Light emitted by the illuminating light sources 11 and reflected from the eye E travels through the puffing nozzle 12, the anterior segment glass plate 13, the chamber glass plate 14, the semitransparent mirror 15, the objective 16, and the semitransparent mirrors 17 and 18, and falls on the CCD camera 19. The objective 16 forms an image of the anterior segment of the eye E on the CCD sensor of the CCD camera 19.

The XY-alignment index projecting optical system 20 has an XY-alignment light source 21 which emits infrared rays, a condenser lens 22, an aperture stop 23, a pinhole plate 24, a dichroic mirror 25, a projection lens 26 disposed on an optical path with its focal point coincided with the pinhole plate 24, the semitransparent mirror 15, the chamber glass plate 14 and the puffing nozzle 12.

Figure 3:
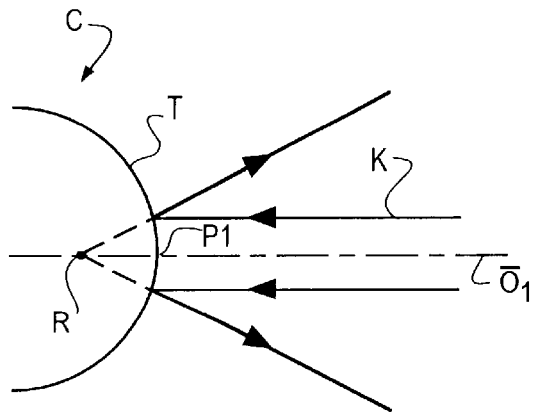
FIG. 3 is a diagrammatic view of assistance in explaining the reflection of an alignment light beam by the cornea when the alignment light beam is projected along the optical axis of the cornea on the cornea by the ophthalmic apparatus shown in FIG. 1.

Infrared rays emitted by the XY-alignment light source 21 are gathered by the condenser lens 22, travel through,the aperture stop 23 and a pinhole formed in the pinhole plate 24, are reflected by the dichroic mirror 25, are collimated by the projection lens 26 in an infrared beam. And the infrared beam is reflected by the semitransparent mirror 15, travels through the chamber glass plate 14 and the puffing nozzle 12, and forms an XY-alignment index light beam K as shown in FIG. 3. As shown in FIG. 3, the XY-alignment index light beam K is reflected so as to form a bright spot R at the midpoint of the vertex P of the cornea C and the center of curvature of the cornea C. The aperture stop 23 and the vertex P of the cornea C are in a conjugate relationship with respect to the projection lens 26.

The fixation target optical system 30 has a fixation target light source 31 which emits visible light, a pinhole plate 32, the dichroic mirror 25, the projection lens 26, the semitransparent mirror 15, the chamber glass plate 14 and the puffing nozzle 12.

Fixation target light rays emitted by the fixation target light source 31 travel through the pinhole of the pinhole plate 32 and the dichroic mirror 25, are collimated by the projection lens 26 in a fixation target beam, and the fixation target beam is reflected by the semitransparent mirror 15, travels through the chamber glass plate 14 and the puffing nozzle 12 and falls on the eye E to form a fixation target mark. The subject fixes the eye E to fix the visual line on the fixation target mark.

The XY-alignment detecting optical system 40 has the puffing nozzle 12, the chamber glass plate 14, the semitransparent mirror 15, the objective 16, the semitransparent mirrors 17 and 18, a semitransparent mirror 41, a pinhole plate 42 and a photodiode 43.

The light beam projected on the cornea C by the XY-alignment index projecting optical system 20 and reflected from the surface T of the cornea C travels through the puffing nozzle 12, the chamber glass plate 14 and the semitransparent mirror 15, and is gathered by the objective 16. A part of the light beam travels through the semitransparent mirror 17. Then, a part of the light beam is reflected by the semitransparent mirror 18. The light beam reflected by the semitransparent mirror 18 travels through the semitransparent mirror 41 and the pinhole 42, and forms in a bright spot R'1 on the photodiode 43.

An XY-alignment detecting circuit 44 detects the condition of alignment with respect to the X- and the Y-direction on the basis of the output of the photodiode 43 and gives the results of detection to a control circuit 80.

The Z-alignment limitation detecting optical system 90 has the semitransparent mirror 41, a pinhole plate 91, a photosensor 92 and a Z-alignment limitation detecting circuit 93.

The semitransparent mirror 41 is disposed between the semitransparent mirror 18 and the photQdiode 43. The photosensor 92 is disposed at a position toward which the semitransparent mirror 41 reflects the light beam. The photosensor 92 has a function of measuring the intensity of incident light, such as a photodiode. The photosensor 92 and the photodiode 43 are in a conjugate relationship with respect to the semitransparent mirror 41. The pinhole plate 91 is disposed right in front of the photosensor 92.

The pinhole plate 91 is made so as to permit the quantity of light more than the predetermined level to fall on the photosensor, when dislocation Ax is so small that it does not influence the accuracy of the Z-alignment detection results The Z-alignment limitation detecting circuit 93 determines whether or not the quantity of light more than the predetermined level is falling on the photosensor 92. When the quantity of light falling on the photosensor 92 is more than the predetermined level, the Z-alignment limitation detecting circuit 93 outputs a signal to the control circuit 80.

Figure 4:
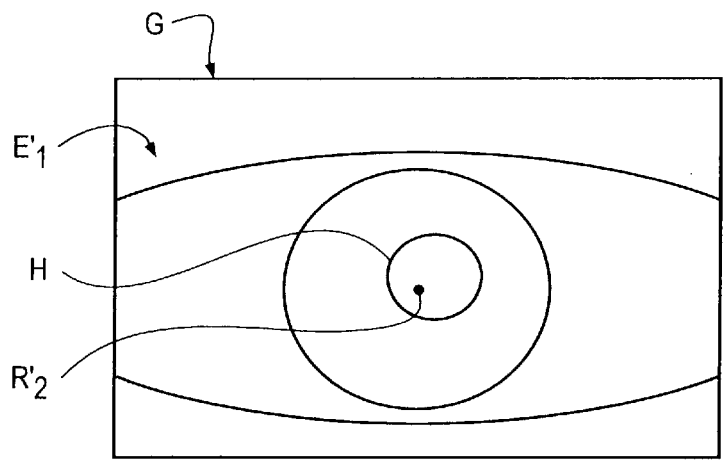
FIG. 4 is a pictorial view of an image of the anterior segment of the eye displayed on the screen of a monitor included in the ophthalmic apparatus shown in FIG. 1.

The reflected light beam which is reflected by the cornea C and traveled through the semitransparent mirror 18 forms a bright spot R'2 on the CCD camera 19. The CCD camera 19 gives an image signal to a monitor. The monitor displays an image E' of the anterior segment of the eye E, and the bright spot R'2 formed by the XY-alignment index light beam on its screen G as shown in FIG. 4. In FIG. 4, indicated at H is an auxiliary alignment mark produced by an image producing means, not shown.

A part of the reflected light beam reflected by the semitransparent mirror 17 toward the cornea deformation detecting optical system 50 travels through the pinhole of a pinhole plate 51 and falls on a photosensor 52. The photosensor 52 is, for example, a photodiode capable of measuring the quantity of the incident light.

The Z-alignment index projecting optical system 60 projects an index light beam for detecting the condition of alignment with respect to Z-direction. The Z-alignment index projecting optical system 60 has a Z-alignment light source 61 which emits infrared rays, a condenser lens 62, an aperture stop 63, a pinhole plate 64, and a projection lens 65 disposed with its focal point coincided with the pinhole plate 64. The Z-alignment index projecting optical system 60 has an optical axis $O_2$.

Figure 5:
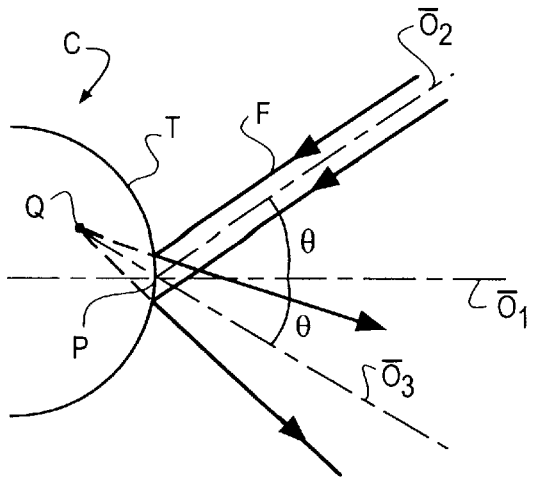
FIG. 5 is diagrammatic view of assistance in explaining the reflection of an alignment light beam obliquely projected on the cornea by the ophthalmic apparatus shown in FIG. 1.

The condenser lens 62 gathers infrared rays emitted by the Z-alignment light source 61, and the gathered infrared rays travel through the aperture stop 63. The gathered infrared rays travel through the pinhole of the pinhole plate 64 in an index light beam F, The index light beam F is collimated by the projection lens 65, falls on the cornea C and is reflected by the corneal surface T so as to form a bright spot Q as shown in FIG. 5. The aperture stop 63 and the vertex P of the cornea C are in a conjugate relationship with respect to the projection lens 65.

The Z-alignment detecting optical system 70 has an image forming lens 71, a cylindrical lens 72 having power in a direction along the Y-axis, and a photosensor (light receiving means) 73. The Z-alignment detecting optical system 70 has an optical axis $O_3$.

The index light beam F projected by the Z-alignment index projecting optical system 60 and reflected by the corneal surface T, is gathered by the image forming lens 71 and is focused by the cylindrical lens 72 in a bright spot Q' on the photosensor 73. The photosensor 73 is a linear photosensor or a photosensor capable of position detection, such as a PSD. Output signals provided by the photosensor 73 are output to a Z-alignment detecting circuit (arithmetic means) 74.

The Z-alignment detecting circuit 74 calculates data representing the positional relation between the main unit S and the cornea C with respect to the Z-direction by a known means, and outputs the calculated data to the control circuit 80.

The bright spot Q and the photosensor 73 are in a conjugate relationship with respect to the image forming lens 71 in an XZ-plane. The vertex P of the cornea C and the photosensor 73 are in a conjugate relationship with respect to the image forming lens 71 and the cylindrical lens 72 in a YZ-plane. The photosensor 73 and the aperture stop 63 are in a conjugate relationship (the power is determined so that the size of an image of the aperture stop 63 is smaller than the size of the photosensor 73), and the reflected light beam from the corneal surface T is able to fall efficiently on the photosensor 73 even if the cornea C is dislocated along the Y-axis. Although efficiency decreases slightly, the same effect can be exercised by projecting a slit light beam having a width along the Y-axis on the cornea C.

Figure 6A:
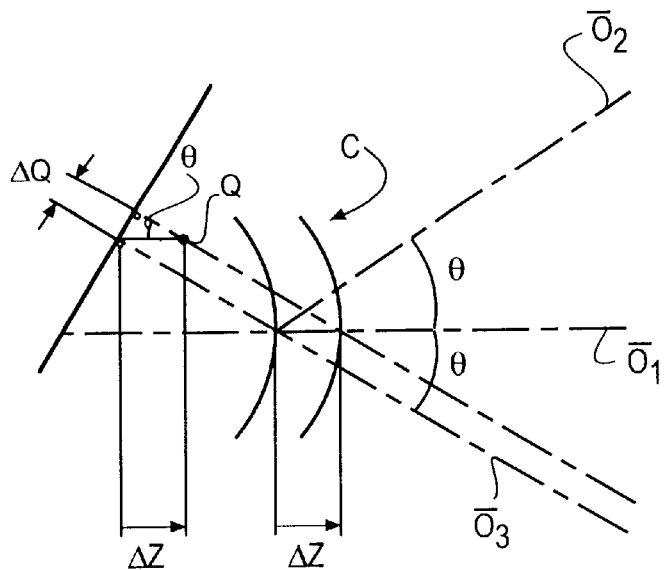
FIG. 6(a) is a diagram of assistance in explaining the relation between a light beam projected on the cornea and a reflected light beam reflected by the cornea in the ophthalmic apparatus shown in FIG. 1 when the cornea is dislocated along a Z-axis from the correct position relative to the ophthalmic apparatus shown in FIG. 1.

As shown in FIG. 6(a), if the cornea C is dislocated by a dislocation AZ along the Z-axis, the bright spot Q' moves on the photosensor 73 by a distance equal to $\Delta Z \times \sin \theta \times m$, where θ is the angle between the optical axes $O_1$ and $O_2$, and the angle between the optical axes $O_1$ and $O_3$, and m is the magnification of the Z-alignrment detecting optical system 70. The dislocation of the cornea C along the Z axis from the correct position can readily be calculated on the basis of the movement of the bright spot Q' on the photosensor 73 if the cornea C is dislocated only along the Z-axis.

Figure 6B:
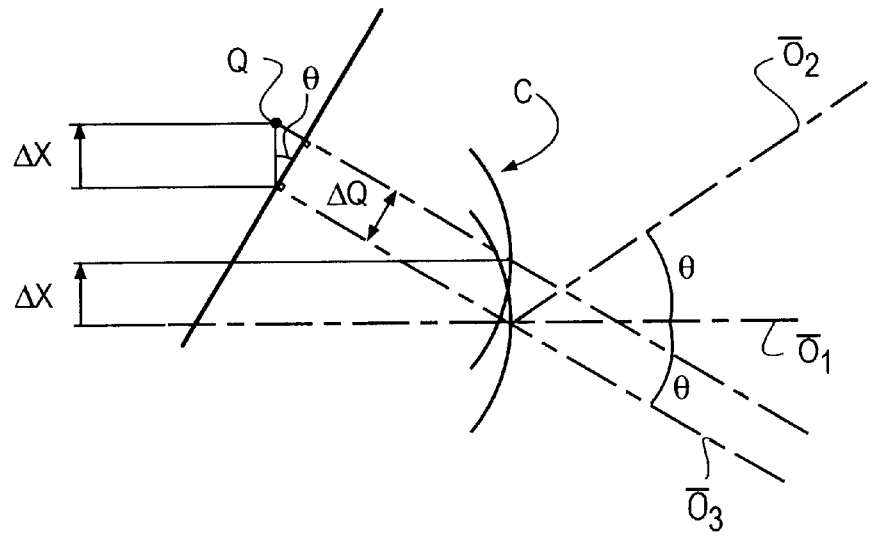
FIG. 6(b) is a diagram of assistance in explaining the relation between a light beam projected on the cornea and a reflected light beam reflected by the cornea in the ophthalmic apparatus shown in FIG. 1 when the cornea is dislocated along an X-axis from the correct position relative to the ophthalmic apparatus shown in FIG. 1.

However, if the cornea C is dislocated by a dislocation AX along the X-axis parallel to a plane including the optical axis $O_2$ of the Z-alignment index projecting optical system 60 and the optical axis $O_3$ of the Z-alignment detecting optical system 70, the bright spot Q' moves by a distance equal to $\Delta X \times \cos \theta \times m$ on the photosensor 73 as shown in FIG. 6(b). Therefore, a large error is introduced into the result of Z-alignment detection if the dislocation ΔX is great.

The apparatus disclosed in JP-A No. Hei 7-23907 corrects the result of Z-alignment detection on the basis of the results of X-alignment detection to solve the foregoing problem. The present invention does not make such correction, but the present invention does not give any permission to display any Z-alignment information unless the dislocation ΔX along the X-axis is reduced to a value which will not affect the accuracy of Z-alignment detection.

Figure 7:
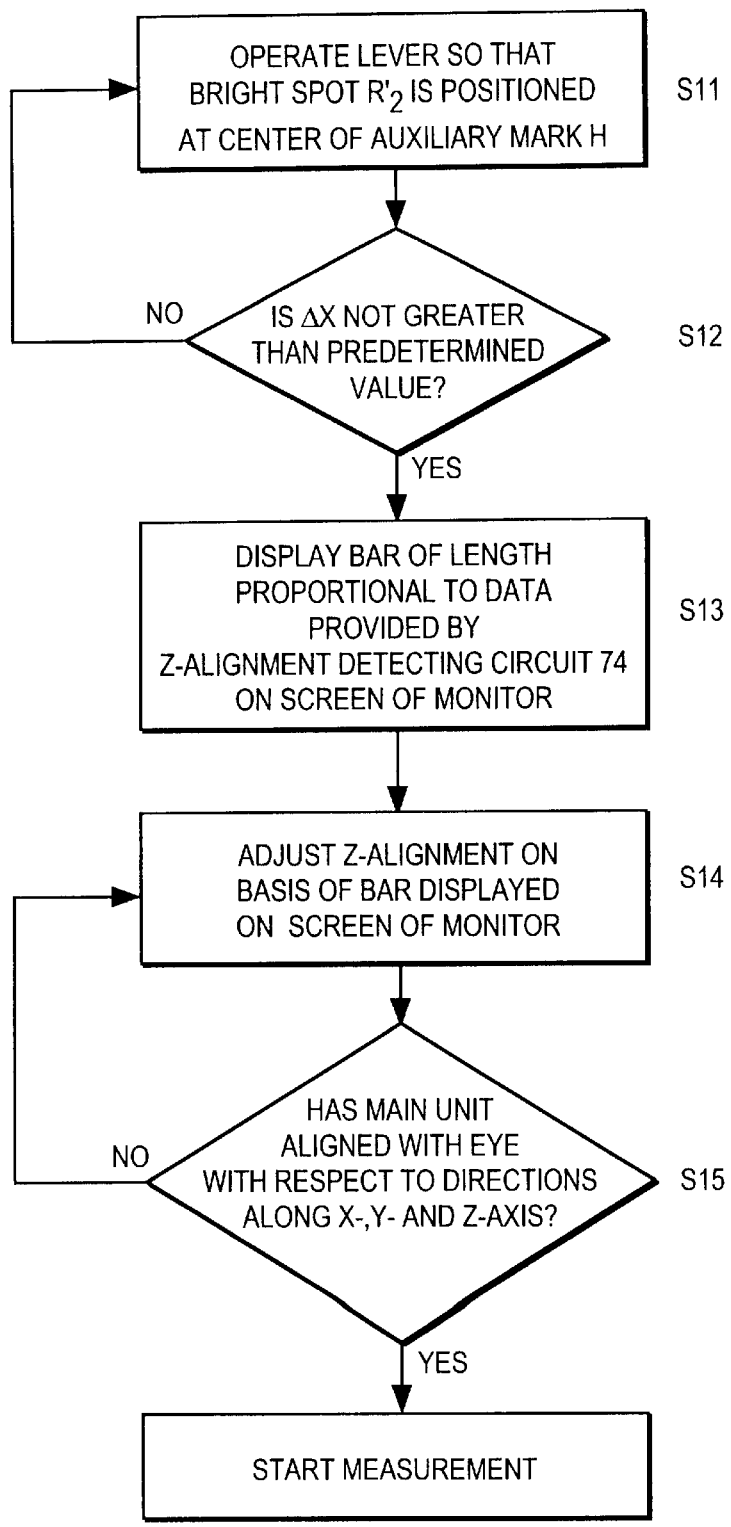
FIG. 7 is a flow chart of a procedure to be carried out by the ophthalmic apparatus shown in FIG. 1.

The operation of the ophthalmic apparatus embodying the present invention will be described with reference to FIG. 7.

The examiner observes an anterior segment image E' of the anterior segment of the subject's eye E and the bright spot R'2 displayed on the screen G of the monitor and operates a control lever, not shown, to move the main unit S in an XY-plane so that the bright spot R'2 is positioned at the center of the auxiliary mark H (step 11). Meanwhile, the Z-alignment limitation detecting circuit 93 determines whether or not the dislocation ΔX is less than a predetermined value, i.e., whether or not the quantity of light fallen on the photosensor 92 is higher than a predetermined level (step 12).

When the dislocation Δx is reduced to a value less than the predetermined value, the control circuit 80 decides that measured data provided by the Z-alignment detecting circuit 74 is reliable, and makes the monitor display a bar of a length proportional to the measured data provided by the Z-alignment detecting circuit 74 on its screen G (step 13).

While the dislocation Δx is greater than the predetermined value, i.e., while the quantity of light fallen on the photosensor 92 is lower than the predetermined level, the control circuit 80 does not make the monitor display any bar. The operation returns to step 11 to continue the operation for positioning the main unit S.

The examiner observes the bar displayed on the screen G of the monitor and moves the main unit S to achieve Z-alignment, so that the bar is shortened (step 14). The XY-alignment detecting circuit 44 and the Z-alignment detecting circuit 74 determine whether or not the main unit S has been aligned with the eye E with respect to the X-, the Y- and the Z-axis, respectively, and give the results of detection to the control circuit 80.

Upon the detection of the alignment of the main unit S with the eye E with respect to the X-, the Y- and the Z-axis (step 15), the control circuit 80 makes the monitor display a message: "ALIGNEMENT OK" on its screen to prompt the examiner to start measurement or makes the main unit S start measurement automatically (step 16).

Thus, consideration is given to the detecting accuracy of the Z-alignment detecting optical system 70, any information about Z-alignment is not displayed while the dislocation AX is large, and information about Z-alignment is displayed after the dislocation ΔX has decreased to a permissible extent. Accordingly, a possibility that the examiner executes faulty operations is reduced and the main unit S can quickly be aligned with the eye E. The Z-alignment limitation detecting optical system 90 permits displaying Z-alignment information upon the detection of the reduction of the dislocation ΔX along the X-axis below the predetermined value.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. An ophthalmic apparatus comprising:

a main unit;

an XY-alignment index light projecting means for projecting an alignment index light beam onto an eye;

an XY-alignment detecting means for detecting the alignment between the main unit and the eye with respect to lateral and vertical directions on the basis of the XY-alignment index light beam reflected from the cornea of the eye;

a Z-alignment index light projecting means for obliquely projecting a Z-alignment index light beam onto the eye;

a Z-alignment detecting means for detecting the alignment between the main unit and the eye with respect to a horizontal direction parallel to the optical axis of the eye on the basis of the Z-alignment index light beam;

a display means for displaying results measured by the Z-alignment detecting means; and a display permitting means for permitting the display means to display information.

* * * * *